United States Patent [19]

Mathur

[11] Patent Number: 5,756,014

[45] Date of Patent: May 26, 1998

[54] HEAT RESISTANT LIPID VESICLES

[75] Inventor: Rajiv Mathur, Sewell, N.J.

[73] Assignee: Igen, Inc., Wilmington, Del.

[21] Appl. No.: 838,633

[22] Filed: Apr. 11, 1997

[51] Int. Cl.$^6$ .............................. B01J 13/02; B01J 13/06
[52] U.S. Cl. ................ 264/4.1; 428/402.2; 428/402.21; 428/402.24
[58] Field of Search ........................ 264/4.1; 428/402.2, 428/402.21, 402.24

[56] References Cited

PUBLICATIONS

ICI Americas Products for Cosmetics and Pharmaceuticals, product literature of ICI Americas Inc., author unknown.

Suginaka et al., Database Caplus, AN 1995:339379 abstracting.

*Primary Examiner*—Jeffrey C. Mullis
*Attorney, Agent, or Firm*—Lahive & Cockfield, LLP

[57] ABSTRACT

Lipid vesicles which remain stable at high temperatures are disclosed. The vesicles contain as a component of their lipid bilayers at least one ethoxylated alcohol having a linear C20–C50 carbon chain. Also disclosed is a method of making the vesicles. The lipid vesicles are useful in forming cosmetic and dermatologic preparations, such as lipstick, which are processed at high temperatures (e.g., at 80° C. or above) during manufacture.

21 Claims, No Drawings

HEAT RESISTANT LIPID VESICLES

BACKGROUND OF THE INVENTION

The present invention relates to lipid vesicles which remain stable at high temperatures. This heat resistance is due in part to the presence of at least one high melting point compound in their lipid bilayers.

As described in U.S. Pat. No. 5,260,065, the contents of which are incorporated by reference herein, blended lipid vesicles made up of at least two surfactants surrounding an aqueous or oil-filled central cavity provide several advantages when used in forming cosmetic preparations. One advantage provided by blended lipid vesicles is the ability to incorporate water and water-soluble compounds into the lipid vesicles which can then be mixed with oily bases to improve their consistency. However, when used in cosmetic or dermatologic compounds which are heated to high temperatures (e.g., 80° C. or higher) during manufacture, these lipid vesicles can break down as the structural components making up their lipid bilayers melt. Accordingly, it is an object of the present invention to provide lipid vesicles which are stable at high temperatures (e.g., above 80° C.) and which do not break down when used in cosmetic or dermatologic compounds which are heated to high temperatures (e.g., 80° C. or higher) during manufacture.

One cosmetic, in particular, which undergoes high temperature processing during manufacture is lipstick. Conventional lipstick manufacture requires heating color pigments and a fatty base, which typically includes waxes, oils and other fats, and uniformly blending the mixture. The base and pigments are generally heated to at least about 85° C. in a steam jacketed kettle. Once molten, they are blended and then molded, allowing for the release of any trapped air. After cooling, the appearance of the lipstick is often refined by passing it through a gas flame to rapidly reheat its surface, leaving a glossy finish.

Due to the high temperature processing used during the manufacture of lipstick and other similar cosmetics, blended lipid vesicles of the prior art have not been practical for use in these compounds. Accordingly, it is another object of the present invention to provide lipid vesicles which can be used in a lipstick preparation.

SUMMARY OF THE INVENTION

The present invention features heat resistant lipid vesicles which can be used in the manufacture of products which are processed at high temperatures, for example, of greater than 80° C. The lipid vesicles are rendered heat stable by incorporating into their lipid bilayers at least one ethoxylated alcohol having a long, substantially linear $C_{20}$–$C_{50}$ carbon chain. The long fatty carbon chain relative to the polar ethoxylated head group of this molecule gives it a high melting point compared to conventional surfactants used to prepare lipid vesicles which typically have carbon chains in the range of $C_{14}$–$C_{22}$. The lipid vesicles of the present invention are therefore particularly useful in the manufacture of oil and/or wax based cosmetics or dermatologics which must be heated to temperatures of about 80° C. or higher to melt the fatty cosmetic base and to achieve sufficient blending with other components such as dyes, oils and fragrances.

Accordingly, in one embodiment, the present invention provides lipid vesicles which have as the major structural components of their lipid bilayers a blend of non-ionic surfactants including a primary surfactant and at least one ethoxylated alcohol having a substantially linear $C_{20}$–$C_{50}$ carbon chain. The lipid bilayers further include a sterol which acts as a membrane modulator to increase the shape and form of the lipid vesicles as well as their stability.

The primary lipid, which constitutes the greatest structural lipid by weight of the bilayers (e.g., 10–20%), can be any suitable non-ionic surfactant known in the art to be useful in forming lipid vesicles. For example, suitable surfactants are disclosed in U.S. Pat. No. 5,260,065, entitled "Blended Lipid Vesicles;" U.S. Pat. No. 5,234,767, entitled "Lipid Hybrid Vesicles;" U.S. Pat. No. 5,439,967 entitled "Propylene Glycol Stearate Vesicles;" U.S. Pat. No. 5,405,615, entitled "Sucrose Distearate Vesicles;" U.S. Pat. No. 5,160,669, entitled "Method of Making Oil Filled Paucilamellar Lipid Vesicles, the contents all of which are incorporated by reference herein. In one embodiment, the primary lipid of the vesicle bilayers is selected from the group consisting of polyoxyethylene glyceryl fatty acid esters (e.g., having 1–10 polyoxyethylene groups), such as polyoxyethylene glyceryl monostearate and polyoxyethylene glyceryl monooleate, $C_{12}$–$C_{18}$ fatty alcohols, $C_{12}$–$C_{18}$ glycol monoesters, $C_{12}$–$C_{18}$ glyceryl mono-and diesters, and mixtures thereof. Preferred primary lipids are selected from the group consisting of $C_{16}$ and $C_{18}$ fatty alcohols, glyceryl mono- and distearate, glyceryl dilaurate, glycol stearate, and mixtures thereof. All of the aforementioned compounds are commercially available.

Sterols useful in forming the lipid bilayers also include any sterol known in the art to be useful as modulators of lipid membranes. Suitable sterols include but are not limited to cholesterol, cholesterol derivatives, hydrocortisone, phytosterol, or mixtures thereof. In one embodiment, the sterol is phytosterol supplied from avocado oil unsaponifiables. The use of this sterol, in particular, to form lipid vesicles is described in U.S. Ser. No. 08/345,223, entitled *Lipid Vesicles Containing Avocado Oil Unsaponifiables,* the contents of which are incorporated by reference herein.

The primary lipid and sterol are mixed with at least one ethoxylated alcohol derived from a primary alcohol having a $C_{20}$–$C_{50}$ average carbon chain, preferably derived from a primary alcohol. In general, the ethoxylated alcohol comprises about 20–80% by weight ethylene oxide (e.g., 2.6–4.0 ethylene oxides per mole) and has a hydroxyl number ranging from about 20–85. The long, substantially linear carbon chain of the ethoxylated alcohol gives it a high melting point and makes the lipid vesicles resistant to breakdown at high temperatures. Preferred ethoxylated alcohols have a melting point of at least about 80° C., more preferably at least about 90° C., and more preferably at least about 100° C. or higher. Such compounds can be purchased from Petrolite Corporation (Tulsa, Okla.) under the brand name UNITHOX™ ethoxylated alcohols. Preferred UNITHOX™ ethoxylated alcohols for use in the present invention include UNITHOX™ 420 having a melting point of 91° C., UNITHOX™ 520 having a melting point of 99° C. and most preferably UNITHOX™ 720 having a melting point of 106° C.

Other high melting point compounds (e.g., having a melting point of at least about 80° C.) may also be used in place of, or in addition to, the ethoxylated alcohol. For example, high melting point lipids, such as ceramides (e.g., phytoceramides) and other sphingolipids (e.g., N-oleoylphytosphingosine), can be used in the lipid bilayers of the vesicles to provide high temperature stability and additional moisture when the vesicles are used in dermatological or cosmetic formulations.

When used in preparations which are processed at high temperatures, such as cosmetic and/or dermatologic preparations, lipid vesicles of the present invention should be made with ethoxylated alcohols which have a melting point which is greater than the highest temperature reached during processing of the preparation. Therefore, the lipid vesicles can be tailored for use in particular products according to the conditions of manufacture of the product. In general, the ethoxylated alcohol or other high melting point compound (e.g., phytoceramides), or combination thereof, is present as approximately 10–25% of the total lipid (by weight) of the vesicles.

The lipid bilayers of the vesicles can further contain one or more secondary surfactants in addition to the primary surfactant(s), the sterol and the ethoxylated alcohol. Suitable secondary surfactants include but are not limited to polyoxyethylene acyl alcohols, $C_{16}$–$C_{18}$ fatty alcohols, quaternary dimethyldiacyl amines, polyoxyethylene sorbitan alcohols, polyglycerols, sorbitan fatty acids esters, fatty acids and their salts, and mixtures thereof. In one embodiment, stearyl alcohol and a polyoxyethylene 10–20 stearyl alcohol are used together as secondary surfactants. Some of the aforementioned compounds are commercially available and be purchased, for example, from ICI Americas, Inc. (Wilmington, Del.) under the trade names BRIJ™ (polyoxyethylene fatty ethers), SPAN™ (sorbitan fatty acid esters), and TWEEN™ (ethoxylated sorbitan fatty acid esters).

In addition to the primary alcohol, sterol and ethoxylated alcohol having a linear $C_{20}$–$C_{50}$ carbon chain derived from a primary alcohol, the lipid vesicles of the present invention can further contain an oil to improve the shape and consistency of the vesicles, as well as to lower the solidification temperature of the products in which the vesicles are used. A wide variety of oils known in the art can be used for this purpose including, but not limited to, castor oil, soybean oil, squalene oil, squalane oil, sesame oil, olive oil, canola oil, corn oil, rapeseed oil, safflower oil, sunflower oil, fish oils, avocado oil, water insoluble vitamins, and mixtures thereof. The oil can also contain a dye to color the vesicles for use in cosmetics.

During manufacture of the vesicles, the oil partitions to the central core of the vesicles while the remaining lipid surfactants are incorporated into the lipid bilayers which surround the core. In one embodiment, the lipid vesicles are paucilamellar vesicles having 2–10 bilayers surrounding an amorphous central cavity.

To form the lipid vesicles of the present invention, the above-described lipid components are blended at a sufficiently high temperature to form an even, homogenous lipid phase. In general, this temperature ranges from about 75°–95° C., preferably about 80°–90° C. In addition, a separate aqueous phase is formed which can contain water-soluble components, such as emulsifiers and preservatives, to further improve the form, consistency and stability of the vesicle preparation. In one embodiment, Polyoxyethylene 20 sorbitan ester (Tween 80) is added to the aqueous phase in an amount which ranges from 1.5–3.0% by weight.

The lipid phase is then shear mixed with the aqueous phase under conditions sufficient to allow formation of the vesicles. This can be achieved using many different techniques known in the art. In a preferred embodiment, the lipid phase and the aqueous phase are shear mixed as described in U.S. Pat. No. 5,163,809, entitled "*Method and Apparatus for Producing Lipid Vesicles*", the disclosure of which is incorporated herein by reference. The term "shear mixing," as used herein, means a shear equivalent to a relative flow of 5–50 m/s through a 1 mm orifice.

The lipid vesicles of the present invention can be used in a wide variety of products, such as cosmetics and dermatologics, to improve the consistency, uniformity and moisture levels of the product. In one embodiment of the invention, the lipid vesicles are used in a lipstick preparation which is formed by blending the vesicles with a fatty lipstick base at a high temperature of 80° C. or greater.

Conventional materials and techniques known in the art for forming lipsticks may be employed using the lipid vesicles of the present invention. In one method, the vesicles are heated to at least about 80°–85° C. with a lipstick base made up of color pigments, waxes, oils and other fats conventionally used in lipstick bases. The lipstick base also can contain emulsifiers to help suspend and disperse the lipid vesicles. In one embodiment, polyethylene glycol hydrogenated castor oil (which can be purchased under the brand name CREMAPHOR™) is added in the base (i.e., exterior to the lipid vesicles) in an amount which is approximately 10% by weight of the base.

To heat the vesicles and lipstick base, a steam jacketed kettle or other suitable apparatus can be used. The mixture is then uniformly blended (allowing for the release of any trapped air), poured into a mold and allowed to cool. Further processing, such as flash flaming, can be employed to improve the gloss and shape of the final lipstick product.

Other uses and modifications of the products and methods of the invention will be apparent from the following description and the claims.

DETAILED DESCRIPTION OF THE INVENTION

The following formulations will illustrate certain embodiments of the invention. These examples are merely illustrative and those skilled in the art may be able to determine other materials and methods which accomplish the same results. Such other materials and methods are included within the scope of the invention.

EXAMPLE 1

In this Example, heat resistant lipid vesicles were made using the procedure described below using ethoxylated alcohols selected from UNITHOX™ 420, 520 or 720. These ethoxylated alcohols contain 2.6–4.0 ethylene oxides per mole and have average molecular weights of 560, 700 and 875, respectively. Vesicles (corresponding to Samples A–C) were also made with varying percentages of Tween 80 (1.5%, 2.0%, 2.5% and 3.0%) and with 10% mineral oil instead of 20% castor oil to determine the effect on the lipid vesicles. Lipid vesicles were formed in all samples, however, the samples listed above as A–C represent the best results in terms of lipid size, shape and homogeneity.

TABLE 1

|  | Sample A | Sample B | Sample C |
| --- | --- | --- | --- |
| Lipid Phase |  |  |  |
| Glyceryl Distearate | 34.2 g | 34.2 g | 34.2 g |
| Stearyl Alcohol | 1.8 g | 1.8 g | 1.8 g |
| Polyoxyethylene 10 Stearyl Alcohol | 18.9 g | 18.9 g | 18.9 g |
| Cholesterol | 9.9 g | 9.9 g | 9.9 g |
| Castor oil | 10.0 ml | 10.0 ml | 10.0 ml |
| UNITHOX ™ 420 | 0.5 g |  |  |
| UNITHOX ™ 520 |  | 1.0 g |  |
| UNITHOX ™ 720 |  |  | 1.0 g |

TABLE 1-continued

|  | Sample A | Sample B | Sample C |
| --- | --- | --- | --- |
| Aqueous phase |  |  |  |
| Deionized water with 3% Polyoxyethylene 20 sorbitan ester (Tween 80) | 35.0 ml | 35.0 ml | 35.0 ml |

Lipid vesicles were formed using the hot loading technique described in U.S. Pat. No. 4,911,928, the disclosure of which is incorporated herein by reference. In this procedure, the lipid phase listed in Table 1 was hydrated with 35.0 ml of deionized water at 70° C. Hydration was achieved by shear mixing the lipid and aqueous phases using two heated 60 cc syringes. However, in this and the following Examples, any method of achieving the proper shear could be used. For example, a flow device such as the NovaMix™ vesicle former is used. The basic details of the NovaMix™ system are described in U.S. Pat. No. 4,895,452, the disclosure of which is incorporated herein by reference.

After processing to form lipid vesicles, the samples were observed under a microscope using polarized light. Sample C containing UNITHOX™ 720 produced the nicest looking, most homogenous population of vesicles of the three samples (i.e., A–C). However, all three samples produced visible lipid vesicles.

EXAMPLE 2

In this Example, heat resistant lipid vesicles were formed at high temperature using the components of Sample C from Example 1 (containing UNITHOX™ 720) (Sample A) with preservatives methyl paraben and propyl paraben (Sample B), and with substitution of 20% of the water with glycerine (Sample C).

TABLE 2

|  | Sample A | Sample B | Sample C |
| --- | --- | --- | --- |
| Lipid Phase |  |  |  |
| Glyceryl Distearate | 11.75 g | 11.75 g | 11.75 g |
| Stearyl Alcohol | 0.6 g | 0.6 g | 0.6 g |
| Polyoxyethylene 10 Stearyl Alcohol | 6.50 g | 6.50 g | 6.50 g |
| Cholesterol | 3.90 g | 3.90 g | 3.90 g |
| Castor oil | 48.0 g | 48.0 g | 48.0 g |
| UNITHOX ™ 720 | 5.0 g | 5.0 g | 5.0 g |
| Aqueous phase |  |  |  |
| Polyoxyethylene 20 sorbitan ester (Tween 80) | 5.50 g | 5.50 g | 5.50 g |
| methyl paraben |  | 0.35 g | 0.35 g |
| propyl paraben |  | 0.04 g | 0.04 g |
| glycerine |  |  | 35.05 g |
| Deionized water | 169.75 g | 169.36 g | 134.31 g |

Lipid vesicles were formed by heating the lipid phase (15.05 g or 17.3 ml) to 95° C. and then hydrating the lipid phase with 35.05 ml of deionized water at 65° C. Hydration was achieved by shear mixing the lipid and aqueous phases using two 60 cc syringes.

After processing to form lipid vesicles, the samples were observed under a microscope using polarized light. A heterogeneous population of vesicles, including many small and medium sized, spherical structures had formed in each sample. Microscopic examination showed smaller sized vesicles in Sample C compared to Samples A and B.

EXAMPLE 3

In this Example, heat resistant lipid vesicles were formed at high temperature using a lower total percentage of surfactants and a higher total percentage of ethoxylated alcohol compared to the vesicles prepared in Examples 1 and 2. Polyoxyethylene 9 glyceryl monostearate (POE 9 GMS) was used in place of the surfactants used in Examples 1 and 2 (e.g., glyceryl distearate, stearyl alcohol, polyoxyethylene 10 stearyl alcohol and polyoxyethylene 20 sorbitan ester). In addition, phytosterol (Generol™ 122N) was used in place of cholesterol.

TABLE 3

|  | Sample A | Sample B | Sample C | Sample D |
| --- | --- | --- | --- | --- |
| Lipid Phase |  |  |  |  |
| POE 9 GMS | 2.0 g | 2.0 g | 1.5 g | 1.0 g |
| Phytosterol | 0.6 g | 0.6 g | 0.6 g | 0.6 g |
| Castor oil | 9.58 g | 9.58 g | 9.58 g | 9.58 g |
| UNITHOX ™ 720 | 1.0 g | 1.25 g | 1.25 g | 1.5 g |
| Aqueous phase |  |  |  |  |
| Deionized water | 36.82 g | 36.57 g | 37.07 g | 37.32 g |

Lipid vesicles were formed by heating the lipid phase to 100° C. and then hydrating the lipid phase with 35.05 ml of deionized water at 95° C. Hydration was achieved by shear mixing the lipid and aqueous phases using two 60 cc syringes.

After processing to form lipid vesicles and cooling, the samples were checked for consistency and observed under a microscope using polarized light.

Samples A and B exhibited a thick, creamy consistency. Sample C was similar to Sample A but not as viscous. Sample D was fluid compared to samples A–C. One day later, the samples exhibited the same consistency.

Under microscopic examination, Samples A–C all contained a substantially uniform population of small, nicely shaped (e.g., spherical) vesicles, with Sample A being the best of the three samples. Sample D had fewer vesicles which were larger than those of Samples A–C. Microscopic examination showed smaller sized vesicles in Sample C compared to Samples A and B.

To test the heat resistance of the vesicles, Samples A–D were placed in a water bath at 85° C. Aliquots from the samples were checked under a microscope at 1.5, 2.5 and 3.5 hours. At 1.5 and 2.5 hours, the samples all appeared the same as they started (i.e., at 0 hours). At 3.5 hours vesicles were still present in all four samples. However, in Samples B–D, other non-vesicle lipid structures (odd-shaped structures) also were visible. Sample A retained the same appearance as it did at the start (i.e., 0 hours). Therefore, it was concluded that Sample A was the best of the four samples in consistency, vesicle size/shape, and heat resistance.

EXAMPLE 4

In this Example, the lipid vesicles from Example 1 were used in lipstick preparations. Each sample A–C was mixed using a vortex mixer in a test tube with melted lipstick base made up of the components shown below in Table 4 at a ratio of 1.0 g (vesicles) to 4.0 g (base). The samples were then placed in a water bath at 80° C. Aliquots were taken after 0, 1, 2, 3, and 4 hours and placed on a slide, diluted with castor oil and observed under a microscope.

At each time point (0, 1, 2, 3, and 4 hours), all three Samples A–C contained dispersed lipid vesicles which had the same appearance as was observed prior to their being mixed and heated with the lipstick base. After 2 hours, a portion of the lipid vesicles in each sample had precipitated and concentrated at the bottom of the test tube, which redispersed upon vortex mixing.

These results demonstrate that lipid vesicles of the present invention made with at least one high melting point ethoxylated alcohol such as UNITHOX™ 420, 520 or 720 remain stable when processed with other cosmetic components at high temperatures of at least 80° C. for an extended period of time.

TABLE 4

| | |
|---|---|
| Castor oil | 2.5 g |
| Lanolin Oil | 12.0 g |
| Wheat Germ Oil | 0.5 g |
| Glyceryl Triacetyl Ricinoleate | 5.0 g |
| Propylene Glycol Ricinoleate | 12.0 g |
| Octyl Dodecanol | 2.0 g |
| Cetyl Ricinoleate | 16.5 g |
| Avocado oil | 3.0 g |
| Candellia Wax | 7.5 g |
| Carnuba Wax | 6.5 g |
| Beeswax | 4.0 g |
| Squalane | 10.0 g |
| $C_{12}$–$C_{15}$ Alkyl Benzoate | 8.5 g |
| Octyl Methoxy Cinnamate | 7.5 g |
| Preservatives | quantity sufficient |
| Vitamin E | 2.0 g |

EXAMPLE 5

In this Example, the lipstick preparation described in Example 4 was modified by adding various Polyethylene glycol (PEG) hydrogenated castor oil preparations (sold under the brand name CREMAPHOR™) to help disperse and maintain suspension of the lipid vesicles in the lipstick base. The PEG hydrogenated castor oil was added at both 10% total base mix (e.g., 2.5 g, as shown in Table 3) and at 5% total base mix (e.g., 1.25 g). The lipid vesicles and lipstick preparation was prepared as described in Example 3 using 1.0 g of vesicles and 9.0 g of base mix with PEG hydrogenated castor oil.

In all four Samples A–D shown in Table 5, the lipid vesicles remained stable and dispersed in the lipstick base after 2 hours at 80° C. In contrast, when adding the PEG hydrogenated castor oils at only 5% total base mix, precipitation and accumulation of vesicles was observed after 1 hour, although the precipitated vesicles were stable and fully formed. These results indicate that addition of emulsifiers such as PEG hydrogenated castor oils can help retain suspension and dispersion of the lipid vesicles of the invention in fatty cosmetic bases during and following manufacture.

TABLE 5

| | Sample A | Sample B | Sample C | Sample D |
|---|---|---|---|---|
| Lipid Phase | | | | |
| Glyceryl Distearate | 2.35 g | 2.35 g | 2.35 g | 2.35 g |
| Stearyl Alcohol | 0.12 g | 0.12 g | 0.12 g | 0.12 g |
| Polyoxyethylene 10 Stearyl Alcohol | 1.3 g | 1.3 g | 1.3 g | 1.3 g |
| Cholesterol | 0.7 g | 0.7 g | 0.7 g | 0.7 g |
| Castor oil | 17.5 ml | 17.5 ml | 17.5 ml | 17.5 ml |
| UNITHOX™ 720 | 1.0 g | 1.0 g | 1.0 g | 1.0 g |
| Aqueous phase | | | | |
| Deionized water with 3% Polyoxyethylene 20 sorbitan ester (Tween 80) | 35.0 ml | 35.0 ml | 35.0 ml | 35.0 ml |
| Lipstick Base (see Table 3) | 22.5 g | 22.5 g | 22.5 g | 22.5 g |
| Polyethylene glycol 60 Hydrogenated Castor oil (CREMAPHOR ™ RH 60) | 2.5 g | | | |
| Polyethylene glycol 40 Hydrogenated Castor oil (CREMAPHOR ™ RH 40) | | 2.5 g | | |
| Polyethylene glycol 35 Hydrogenated Castor oil (CREMAPHOR ™ EL) | | | 2.5 g | |
| Polyethylene glycol 7 Hydrogenated Castor oil (CREMAPHOR ™ WO-7) | | | | 2.5 g |
| Lipid Vesicles | 2.78 g | 2.78 g | 2.78 g | 2.78 g |

EQUIVALENTS

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of this invention and are encompassed by the following claims.

What is claimed is:

1. A lipid vesicle having one or more lipid bilayers comprising:
   (a) a primary surfactant selected from the group consisting of polyoxyethylene glyceryl monostearate, polyoxyethylene glyceryl monooleate, $C_{12}$–$C_{18}$ fatty alcohols, $C_{12}$–$C_{18}$ glycol monoesters, $C_{12}$–$C_{18}$ glyceryl mono-and diesters, and mixtures thereof;
   (b) a sterol; and
   (c) at least one ethoxylated alcohol having a linear $C_{20}$–$C_{50}$ carbon chain and a melting point of at least 80° C.

2. The lipid vesicle of claim 1 wherein the primary surfactant is selected from the group consisting of $C_{16}$–$C_{18}$ fatty alcohols, glyceryl mono- and distearate, glyceryl dilaurate, glycol stearate, and mixtures thereof.

3. The lipid vesicle of claim 1 wherein the sterol is selected from the group consisting of cholesterol, cholesterol derivatives, hydrocortisone, phytosterol, and mixtures thereof.

4. The lipid vesicle of claim 3 wherein the phytosterol is supplied from avocado oil unsaponifiables.

5. The lipid vesicle of claim 1 wherein the ethoxylated alcohol comprises 20–80% by weight ethylene oxide.

6. The lipid vesicle of claim 1 wherein the ethoxylated alcohol has a melting point of at least 80° C.

7. The lipid vesicle of claim 1 further comprising at least one secondary surfactant selected from the group consisting of polyoxyethylene acyl alcohols, $C_{16}$–$C_{18}$ fatty alcohols, quaternary dimethyldiacyl amines, polyoxyethylene sorbitan alcohols, polyglycerols, sorbitan fatty acid esters, fatty acids and their salts, and mixtures thereof.

8. The lipid vesicle of claim 7 wherein the secondary surfactant is selected from the group consisting of stearyl alcohol and polyoxyethylene 10–20 stearyl alcohols.

9. The lipid vesicle of claim 1 further comprising an oil.

10. The lipid vesicle of claim 9 wherein the oil is selected from the group consisting of castor oil, soybean oil, squalene oil, squalane oil, sesame oil, olive oil, canola oil, corn oil, rapeseed oil, safflower oil, sunflower oil, fish oils, avocado oil, water insoluble vitamins, and mixtures thereof.

11. The lipid vesicle of claim 1 wherein the lipid vesicle is paucilamellar.

12. A lipstick preparation comprising a blend of the lipid vesicle of claim 1 and a fatty lipstick base containing at least one dye.

13. A method of preparing lipstick comprising the steps of:
   (a) mixing the lipid vesicle of claim 1 with a fatty lipstick base comprising at least one dye at a temperature of 80° C. or higher;
   (b) moulding the mixture; and
   (c) allowing the mixture to cool.

14. A lipid vesicle having one or more lipid bilayers comprising:
   (a) a primary surfactant selected from the group consisting of glyceryl mono- and distearate, glyceryl dilaurate, glycol stearate, polyoxyethylene glyceryl monostearate, polyoxyethylene glyceryl monooleate, and $C_{16}$–$C_{18}$ fatty alcohols;
   (b) at least one secondary selected from the group consisting of stearyl alcohol and polyoxyethylene 10–20 stearyl alcohols;
   (b) a sterol selected from the group consisting of cholesterol and phytosterol; and
   (c) at least one ethoxylated alcohol having a linear $C_{20}$–$C_{50}$ carbon chain and a melting point of at least 80° C.

15. A method of preparing a lipid vesicle comprising the steps of:
   (a) forming a lipid phase comprising a primary surfactant selected from the group consisting of polyoxyethylene glyceryl monostearate, polyoxyethylene glyceryl monooleate, $C_{12}$–$C_{18}$ fatty alcohols, $C_{12}$–$C_{18}$ glycol monoesters, $C_{12}$–$C_{18}$ glyceryl mono-and diesters, and mixtures thereof; a sterol; and at least one ethoxylated alcohol having a linear $C_{20}$–$C_{50}$ carbon chain and a melting point of at least 80° C.;
   (b) forming and aqueous phase; and
   (c) shear mixing the lipid phase and the aqueous phase to form a lipid vesicle.

16. The method of claim 15 wherein the primary surfactant is selected from the group consisting of $C_{16}$–$C_{18}$ fatty alcohols, glycol stearate, glyceryl mono- and distearate, glyceryl dilaurate, polyoxyethylene glyceryl monostearate, and mixtures thereof.

17. The method of claim 15 wherein the sterol is selected from the group consisting of cholesterol, cholesterol derivatives, hydrocortisone, phytosterol, and mixtures thereof.

18. The method of claim 15 wherein the ethoxylated alcohol has a melting point of at least 80° C.

19. The method of claim 15 wherein the lipid phase further comprises at least one secondary surfactant selected from the group consisting of polyoxyethylene acyl alcohols, $C_{16}$–$C_{18}$ fatty alcohols, quaternary dimethyldiacyl amines, polyoxyethylene sorbitan alcohols, polyglycerols, sorbitan fatty acids esters, fatty acids and their salts, and mixtures thereof.

20. The method of claim 15 wherein the lipid phase further comprises an oil.

21. The method of claim 15 wherein the aqueous phase comprises at least one emulsifier.

* * * * *